Figure 5:
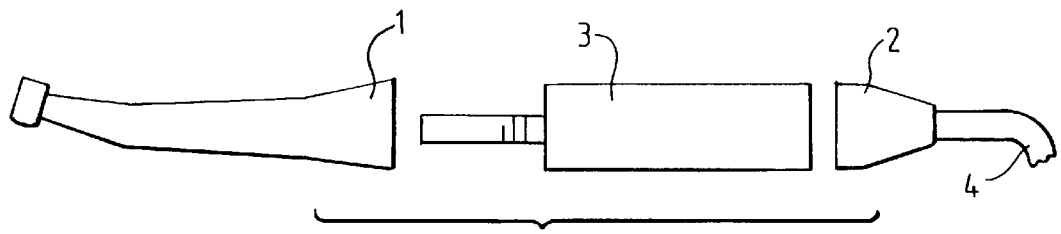

United States Patent [19]
Knorpp et al.

[11] Patent Number: 6,132,213
[45] Date of Patent: Oct. 17, 2000

[54] DENTAL TOOL HOLDER

[75] Inventors: Ernst Knorpp; Wolfgang Thaler, both of Leutkirch, Germany

[73] Assignee: Kaltenbach & Voigt GmbH & Co., Biberach, Germany

[21] Appl. No.: 09/091,433

[22] PCT Filed: Oct. 21, 1997

[86] PCT No.: PCT/EP97/05813

§ 371 Date: Jun. 18, 1998

§ 102(e) Date: Jun. 18, 1998

[87] PCT Pub. No.: WO98/18401

PCT Pub. Date: May 7, 1998

[30] Foreign Application Priority Data

Oct. 25, 1996 [DE] Germany .......................... 196 44 491

[51] Int. Cl.[7] .................................................. A61C 1/00
[52] U.S. Cl. ............................................ 433/131; 433/126
[58] Field of Search ................................... 433/126, 127, 433/129, 131, 132

[56] References Cited

U.S. PATENT DOCUMENTS

| | | | |
|---|---|---|---|
| 950,759 | 3/1910 | Weiner | 433/131 |
| 3,900,952 | 8/1975 | Landgraf et al. | 32/27 |
| 4,235,595 | 11/1980 | Arnegger | 433/131 |
| 4,251,212 | 2/1981 | Worschischek et al. | 433/126 |
| 4,278,907 | 7/1981 | Landgraf et al. | 310/191 |
| 4,279,596 | 7/1981 | Weber | 433/126 |
| 4,486,176 | 12/1984 | Tardieu et al. | 433/133 |
| 4,937,485 | 6/1990 | Mihalko | 310/208 |

FOREIGN PATENT DOCUMENTS

| | | |
|---|---|---|
| 0 012 871B | 11/1979 | European Pat. Off. . |
| 2 257 301A | 11/1972 | Germany . |
| 27 56 011A | 12/1978 | Germany . |
| 28 34 099A | 2/1980 | Germany . |
| 32 37 197 | 4/1983 | Germany . |

*Primary Examiner*—John J. Wilson
*Attorney, Agent, or Firm*—Marshall, O'Toole, Gerstein, Murray & Borun

[57] ABSTRACT

Dental handpiece with an instrument section (1) for accepting a dental tool and with a second, hose section (2) which is capable of being detachably coupled to the instrument section and to which a media delivery line for the delivery of certain supply media for operation of the dental tool is capable of being linked, said dental tool being operated by a drive motor (3). The drive motor comprises a stator (9) and a rotor (5). The rotor (5) of the drive motor (3) is arranged in the instrument section (1) separate from the stator (9), the stator (9) of the drive motor (3) being arranged in the hose section (2). By virtue of the partial integration, in accordance with the invention, of the drive motor, the weight of the dental handpiece is diminished and the ease of handling of the dental handpiece is improved. In addition, higher working speeds of the dental tool can be achieved.

24 Claims, 3 Drawing Sheets

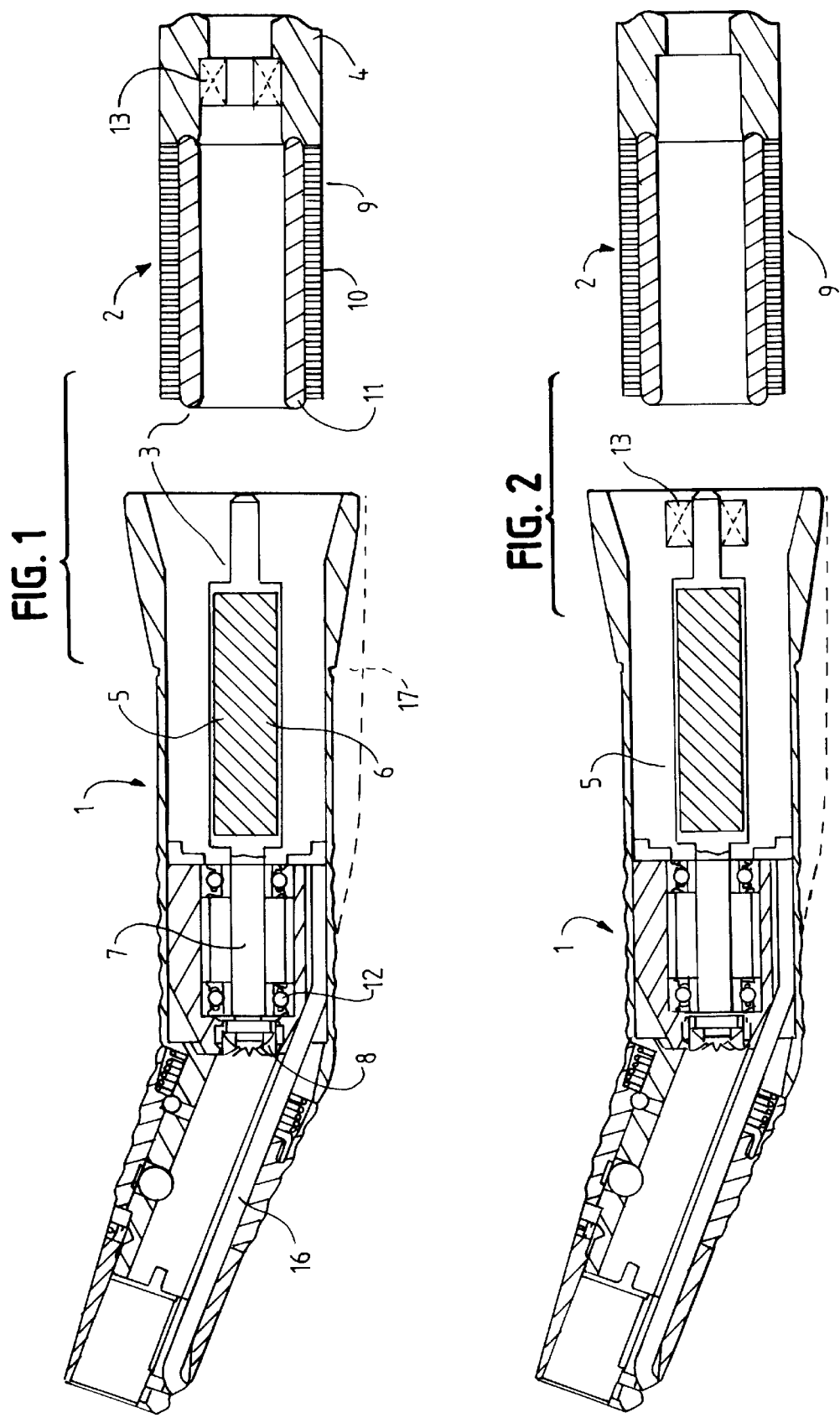

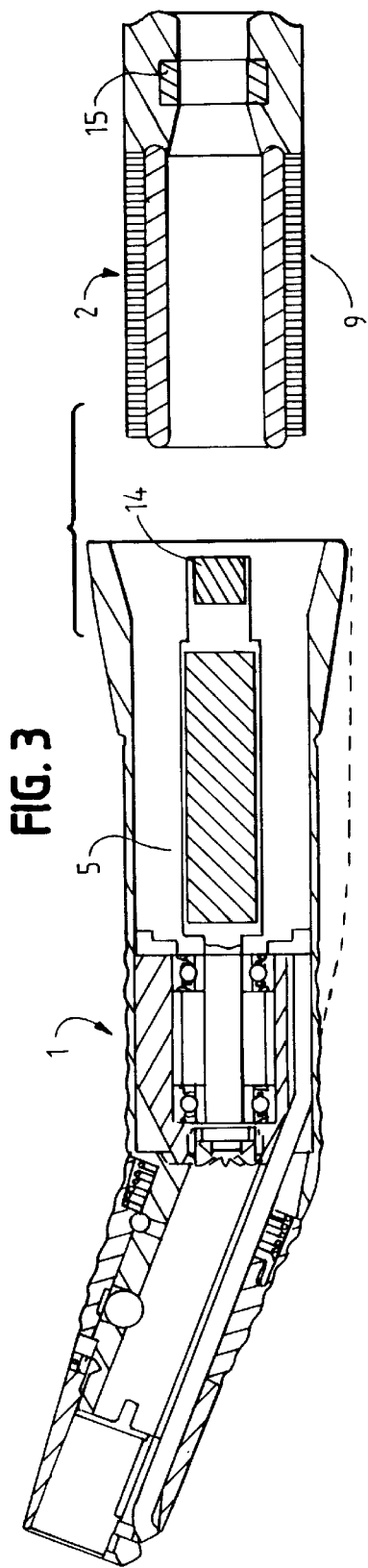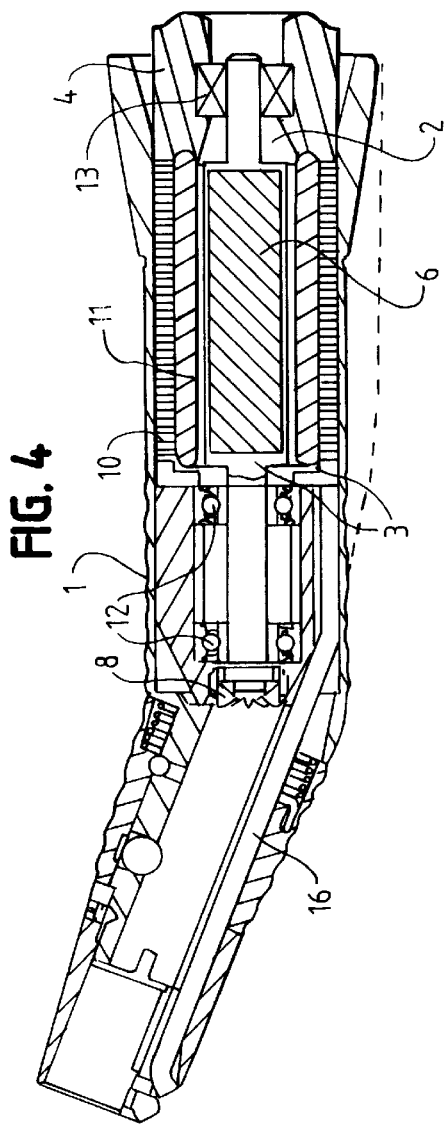

DENTAL TOOL HOLDER

The present invention relates to a dental handpiece for medical or technical purposes.

In particular, the invention relates to the arrangement of a drive system in the dental handpiece, said drive system having a drive motor for driving a dental tool that can be operated with the dental handpiece.

Dental handpieces generally comprise an instrument section for accepting a dental tool, a turbodrill for example, a drive motor for driving the rotating dental tool and a hose section with a media delivery hose for delivering certain supply media for operation of the dental tool, such as, for example, current, spray air or cooling air, spray water, etc. With regard to the construction of the dental handpiece, essentially a distinction is made between two different types of construction.

As shown in FIG. 5, the instrument section 1, the drive motor 3 and the hose section 2 with the media delivery hose 4 may be present in the form of individual components which are directly coupled in series by being fitted onto one another. This construction consequently has three coupling points between the instrument section 1 and the hose section 2 and also between the drive motor 3 and each of the two sections 1 and 2. A construction of this type is known from, for example, DE 28 34 099 C2 or EP 0 012 871 B1.

Figure 6:
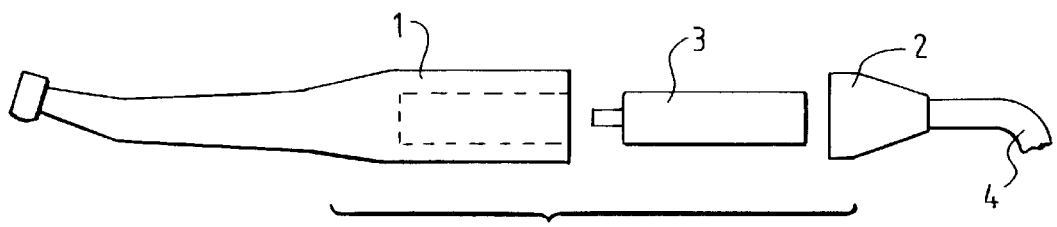

The second type of construction of the dental handpiece is represented in FIG. 6. In this case the drive motor 3 is a motor cartridge retained in a hollow space formed by the instrument section 1 and the hose section 2. For this purpose the instrument section possesses a casing overlapping the drive motor 3 with integrated supply lines for accepting the supply media delivered from the media delivery hose, said casing and the supply lines of the instrument section 1 being guided as far as the hose section 2.

However, the known types of construction are problematic in many respects. For instance, as a result of the large overall length owing to the type of design and as a result of the relatively high weight of the dental handpiece, handling of the handpiece is made difficult, since the centre of gravity of the handpiece is shifted towards the hose. Precisely for dental operations, however, sensitive and easy handling of the dental handpiece is required. The many coupling points or points of separation within the dental handpiece are critical with regard to the hygiene requirements. In addition, these points of separation make secure passage of the supply media difficult, since slightly leaky points may arise. Furthermore, the rotary capacity of the handpiece that is necessary for working in the mouth of a patient is hindered, since rotation always has to be effected via the coupling points of the drive motor. Since the motor shaft of the drive motor necessarily has to be coupled mechanically to a shaft that is present in the instrument section in order to operate the dental tool, as a result the maximum rotary speed is limited and the handpiece tends to vibrate and to generate noise. Moreover, with the known types of construction the requisite different rotary-speed and power ranges—ie, low rotary-speed ranges with high torque requirements and high rotary-speed ranges with low torque requirements—can only be achieved by use being made of a plurality of different and exchangeable instrument sections having the appropriate graduations of transmission, as a result of which, however, the costs of the overall system increase considerably. Finally, with the known types of construction each drive part has its own bearing system. As a result of this, however, the susceptibility of the dental handpiece to wear increases correspondingly and additional heating of the components of the handpiece may occur as a result of bearing friction.

The object underlying the present invention is therefore to create a dental handpiece with which the aforementioned disadvantages are generally avoided.

In particular, the object underlying the present invention is to create a dental handpiece with which, as a result of reducing the number of points of separation, the hygiene and cleaning capacity are improved, the overall weight is diminished and the ease of handling is improved, with the manufacturing costs of the dental handpiece as a whole being reduced at the same time.

In addition, different rotary-speed and power ranges of a dental tool to be operated are to be achievable with one and the same instrument section in order to reduce the capital expenditure for a user—ie, the plurality of different transmission variants and transmission ratios is to be cut down to a minimum.

According to the invention this object is achieved by means of a dental handpiece as disclosed herein.

According to the invention the drive motor is partially integrated within the instrument section of the dental handpiece. The rotating and hence power-transmitting region of the drive motor—ie, the rotor—is arranged in the instrument section, whereas the static region—ie, the stator with the stator winding—is arranged in the hose section separate from the rotor. The rotor is supported with its rear end in the hose section, for example by means of a bearing arrangement which is appropriately provided.

In principle the reverse is also possible—ie, the stator arranged in the instrument section and the rotor in the hose section. This alternative may advantageously find application in the case of a collector motor. For the sake of simplicity, further developments of the invention are described below on the basis of the first-mentioned possibility only.

As a result of joining or plugging the two sections of the dental handpiece together the stator of the hose section is pushed over the rotor of the instrument section, so that a dental handpiece is obtained having a virtually integrated drive motor.

The construction according to the invention of the dental handpiece is advantageous in many respects.

As a result of the arrangement of the stator in the hose section the actual cost-intensive parts of the drive motor are integrated within the-hose section and may be used equally well for the most diverse designs of the instrument section with differing speed-increasing or speed-reducing ratios, so that these parts only have to be procured once. By virtue of the construction according to the invention there is now one point of separation between the instrument section and the hose section, so that the coupling and sealing provision for the supply lines is improved and cleaning of the handpiece is alleviated. In addition, the stator parts which are critical in connection with the sterilisation of the handpiece are no longer arranged in the instrument section but in the hose section, there being no need for the hose section to be sterilised. Consequently, hygiene is clearly improved overall. Finally, by reason of the one point of separation that is now present the dental handpiece according to the invention has considerably improved rotary capacity as well as a reduced overall length and a reduced overall weight.

Further advantages of the invention arise as a result of the fixed seating of the rotor of the drive motor on the first transmission stage of the instrument section, since in comparison with a separate motor two ball bearings can be eliminated. Since coupling of the rotor of the drive motor to the first transmission stage of the instrument section is no longer necessary, the coupling noises are diminished and the manufacturing costs are reduced. As a result of the omission of this coupling and the saving of bearing points, altogether a clearly higher driving speed can be accomplished, as a result of which smaller transmission ratios in order to achieve the same rotary speed of the tool are in turn made possible, thus increasing the operational reliability. As a result of the extension of the rotary-speed range the large number of different instrument transmissions previously necessary can likewise be reduced. Since, in accordance with the invention, the rotor of the drive motor is arranged within the instrument section, the dental handpiece has a shorter overall length and a diminished weight and also, consequently, improved ease of handling.

According to advantageous embodiments of the invention the rotor and/or the stator can be taken out of the instrument section or hose section, respectively, of the dental handpiece and exchanged for another rotor with, for example, a different rotor magnet or, respectively, another stator with a different stator winding, so that different rotary-speed and power ranges can be achieved with the use of the same instrument without the remaining construction of the dental handpiece having to be changed. Likewise it is conceivable to exchange only the magnet of the rotor for another magnet of different permeability.

Finally, in accordance with the invention the stator winding of the drive motor may also be designed to be controllable in order to achieve different rotary speeds with respect to the electrical power supplied to the stator winding. For this purpose the stator winding may also have several individual coils connected in parallel which are capable of being switched on and off separately, so that the rotary speed of the drive motor can be controlled by optional connection of the individual stator coils.

Further advantageous embodiments of the invention are described in the subclaims.

The invention is described below with reference to the drawing on the basis of preferred embodiment examples.

FIG. 1 shows a first embodiment example of the present invention wherein the instrument section is separate from the hose section, FIG. 2 shows a second embodiment example of the present invention wherein the instrument section is separate from the hose section, FIG. 3 shows a third embodiment example of the present invention wherein the instrument section is separate from the hose section, FIG. 4 shows the first embodiment example of the present invention in the assembled state, FIG. 5 shows a known dental handpiece, and FIG. 6 shows another known dental handpiece.

FIG. 1 shows in principle the construction of the dental handpiece according to the invention. The dental handpiece according to the present invention basically comprises two casing sections, namely the instrument section 1 which serves to accept (for example, by fitting on) a rotating dental tool (a turbodrill for example) and the hose section 2 with an extension piece for a media delivery hose 4 which is either attached to the hose section 2 directly or is capable of being coupled thereto (for example, capable of being screwed on). The media delivery line 4 serves to deliver various supply media in order to operate the dental tool, such as, for example, current (for an illumination device and the electric drive motor 3), cooling air, spray air or spray water.

The drive motor 3, which comprises a rotating region (rotor) 5 and a static region (stator) 9, serves to drive the dental tool. The drive motor 3 preferably has no collector—ie, it is an asynchronous motor or a brushless d.c. motor, for example. The rotor 5 comprises a permanent magnet 6 and a motor shaft 7. The stator comprises a stator sheet packet 10 and a stator winding 11. According to the invention the motor shaft 7 is seated immediately on the first transmission stage 8 of the instrument section which serves to transmit the torque of the motor shaft 7 to the dental tool to be operated. The rotor 5 is integrated within the instrument section 1 in self-supporting manner. The stator 9 is separate from the rotor 5 and arranged in the hose section 2. Both rotor 5 and stator 9 may be arranged or integrated within the respective section 1 or 2 either permanently or exchangeably. In particular, the stator 9 may be attached within the hose section 2 via plug contacts. If rotor 5 and/or stator 9 are arranged in the instrument section 1 or hose section 2 so as to be capable of being taken out, the rotor 5 or the stator 9 may advantageously be exchanged for another rotor with, for example, a different rotor magnet or, respectively, another stator with a different stator winding, so that different rotary-speed and power ranges can be achieved with the use of the same instrument without the construction of the dental handpiece otherwise having to be changed. Similarly, the rotor 5 may be constructed in such a way that only the rotor magnet 6 is exchangeable for a rotor magnet of different permeability.

In order, furthermore, to be able to achieve different rotary-speed ranges with one and the same handpiece or the same instrument and hose sections, the supply of electrical power to the stator winding 11 of the stator 9 may be controllable. The stator winding 11 may also be divided up into several individual coils that can be activated separately and independently of one another, so that the electrical power supplied to the stator winding 11 can be controlled by switching on and off certain individual coils. In this manner one and the same dental handpiece can be switched over to different rotary-speed ranges.

After assembly of the sections 1 and 2 the rotor 5 is borne and supported with its rear end also in the hose section 2. According to FIG. 1 a ball bearing 13 is provided in the hose section 2 for this purpose. As a result of pushing the two sections 1 and 2 together, on the one hand the stator 9 is pushed over the rotor 5 and on the other hand the rear end of the rotor 5 is pushed into the ball bearing 13. In order also to support the rotor 5 additionally when the sections 1 and 2 are not assembled and the rotor 5 is therefore not supported in the hose section 2, additional ball bearings 12 which support the motor shaft 7 may optionally be provided in the instrument section.

The instrument section 1 has several supply lines 16 in order to deliver the supply media delivered from the media delivery line 4 to the dental tool to be operated. The instrument section 1 presents on its underside an asymmetrically designed casing shape by way of additional free space for the supply lines 16. The supply lines 16 integrated within the instrument section 1 extend in the assembled state as far as the hose section 2, so that as a result of pushing the sections 1 and 2 together the supply lines 16 of the instrument section 1 are directly connected to the media delivery line 4. Alternatively the hose section 2 may also have correspondingly formed supply lines (not shown) which on the one hand are linked to the media delivery line 4 and on the other hand, as a result of pushing the sections 1 and 2 together, are connected to the corresponding supply lines 16 of the instrument section 1 in order to ensure direct and secure transmission of the supply media.

FIG. 2 shows a second embodiment example of the dental handpiece according to the invention, the second embodiment example differing from the embodiment example shown in FIG. 1 only in that the ball bearing 13 for supporting and bearing the rear part of the rotor 5 in the hose section 2 is attached to the rotor 5.

In advantageous manner use may also be made of an air bearing or slide bearing by way of bearing for the rear end of the rotor 5 in the hose section 2. In particular, use may be made of magnetic bearing which is represented in FIG. 3. The static part 15 of the magnetic bearing is connected to the hose section 2 and the rotating part 14 of the magnetic bearing is connected to the rotor 5 of the drive motor.

FIG. 4 shows the dental handpiece according to the invention in the assembled state. It is evident that, according to the invention, by plugging the instrument section 1 and the hose section 2 together a compact handpiece is obtained having a drive motor 3 which, in principle, is integrated.

We claim:

1. A dental handpiece, with a first section (1) for accepting a dental tool, with a second section (2) which is capable of being detachably coupled to the first section (1) and to which a media delivery line (4) for the delivery of certain supply media for operation of the dental tool is capable of being linked, and with a drive motor (3) for driving the dental tool, said drive motor (3) comprising a rotating region (5) and a static region (9) and being arranged, after the first and second sections (1; 2) have been joined together, in a hollow space formed by the first section (1) and the second section (2), wherein in the separated state of the first and second sections (1; 2) the rotating region (5) of the drive motor (3) is arranged in the first section (1) and the static region (9) of the drive motor (3) is arranged in the second section (2) or conversely.

2. A dental handpiece of claim 1, wherein the rotating region (5) and the static region (9) of the drive motor (3) are arranged in such a way that as a result of joining the first and second sections (1; 2) together the static region (9) of the drive motor (3) is pushed over the rotating region (5) of the drive motor (3).

3. A dental handpiece of claim 1, wherein the drive motor (3) is a motor without a collector.

4. A dental handpiece of claim 3, wherein the drive motor (3) is an asynchronous motor or a brushless d.c. motor.

5. A dental handpiece of claim 1, wherein the rotating region (5) of the drive motor (3) is exchangeably arranged in the first section (1).

6. A dental handpiece of claim 5, wherein the rotating region (5) of the drive motor (3) comprises a permanent magnet (6) which is exchangeable.

7. A dental handpiece of claim 1, wherein the rotating region (5) of the drive motor (3) comprises, at one end facing the first section (1), a rotating motor shaft (7) which is arranged in the first section (1) in self-supporting manner.

8. A dental handpiece of claim 1, wherein the rotating region (5) of the drive motor (3) comprises, at its end facing the first section (1), a rotating motor shaft (7) which is supported in the first section (1) by means of a bearing (12).

9. The dental handpiece of claim 1, wherein said bearing is a ball bearing.

10. A dental handpiece of claim 1, wherein in the assembled state of the first and second sections (1; 2) the end of the rotating region (5) of the drive motor (3) facing the second section (2) is supported in the second section (2).

11. A dental handpiece of claim 10, wherein the end of the rotating region (5) of the drive motor (3) facing the second section (2) is supported by means of a rotor bearing (13).

12. A dental handpiece of claim 11, wherein the rotor bearing (13) is attached to the rotating region (5) of the drive motor (3).

13. A dental handpiece of claim 12, wherein the static region (9) of the drive motor (3) has several windings (11) which are capable of being connected separately from one another.

14. A dental handpiece of claim 11, wherein the rotor bearing (13) is arranged in the second section (2).

15. A dental handpiece of claim 11, wherein the rotor bearing (13) is a ball bearing.

16. A dental handpiece of claim 11, wherein the rotor bearing (13) is an air bearing or slide bearing.

17. A dental handpiece of claim 11, wherein the rotor bearing (13) is a magnetic bearing, the rotating part (14) of which is attached to the rotating region (5) of the drive motor (3) and the static part (15) of which is attached within the second section (2).

18. A dental handpiece of claim 1, wherein the static region (9) of the drive motor (3) is exchangeably arranged in the second section (2).

19. A dental handpiece of claim 1, wherein the first section (1) has supply lines (16) for the supply media, said supply lines being directly connected to the media delivery line as a result of assembly of the first and second sections (1; 2), so that the supply media are capable of being delivered immediately to the first section (1) from the media delivery line (4) which is linked to the second section (2).

20. A dental handpiece of claim 19, wherein the supply lines (16) are provided for the supply media which are constituted by current and/or spray air and/or spray water and/or cooling air.

21. A dental handpiece of claim 1, wherein the first and second sections (1; 2) have appropriately formed supply lines (16) for the supply media, said supply lines being connected to one another as a result of assembly of the first and second sections (1; 2), the supply lines pertaining to the second section (2) being in addition connected to the media delivery line (4), so that via the supply lines (16) pertaining to the second and first sections (1) the supply media are capable of being delivered to the dental tool from the media delivery line (4) which is linked to the second section (2).

22. A dental handpiece of claim 1, wherein the media delivery line (4) is directly attached to the second section (2).

23. A dental handpiece of claim 1, wherein the static region (9) of the drive motor (3) is capable of being controlled in order to achieve different rotary speeds of the rotating region (5) of the drive motor (3).

24. A dental handpiece of claim 1, wherein the rotating region (5) of the drive motor (3) is directly connected to a transmission stage of the instrument section (1), said transmission stage serving to transmit the torque of the rotating region (5) to the dental tool.

* * * * *